United States Patent [19]

Krimm et al.

[11] Patent Number: 4,511,722

[45] Date of Patent: Apr. 16, 1985

[54] PROCESS FOR PREPARING CYCLIC N-VINYLACYLAMINES

[75] Inventors: Heinrich Krimm; Hans-Josef Buysch, both of Krefeld; Peter M. Lange, Leverkusen; Reinhold Klipper, Cologne, all of Fed. Rep. of Germany

[73] Assignee: Bayer Aktiengesellschaft, Leverkusen, Fed. Rep. of Germany

[21] Appl. No.: 466,807

[22] Filed: Feb. 16, 1983

[30] Foreign Application Priority Data

Feb. 26, 1982 [DE] Fed. Rep. of Germany ....... 3207031

[51] Int. Cl.$^3$ ................. C07D 263/20; C07D 209/40; C07D 207/12; C07D 233/32
[52] U.S. Cl. .................................... 548/231; 548/221; 548/226; 548/305; 548/308; 548/317; 548/480; 548/543; 548/545; 546/242; 544/105; 544/173; 544/285; 544/309; 544/315

[58] Field of Search ............... 548/226, 229, 232, 308, 548/309, 520, 544, 545, 221, 231, 227, 305, 317, 480, 543; 544/105, 242, 296, 173, 285, 309, 315; 546/242

[56] References Cited

U.S. PATENT DOCUMENTS 2,276,840  3/1942  Hanford et al. ..................... 548/480
2,818,362  12/1957  Drechsel ............................. 548/231

Primary Examiner—Nicholas S. Rizzo
Assistant Examiner—S. A. Gibson
Attorney, Agent, or Firm—Sprung Horn Kramer & Woods

[57] ABSTRACT

Cyclic N-vinylacylamines are prepared by heating carbonic acid esters of cyclic N-2-hydroxyethylacylamines in the presence of a catalytic amount of alkali or alkaline earth metal compound having an alkaline reaction and subsequently distilling the reaction mixture.

Cyclic N-vinylacylamines are valuable precursors for preparing plant protection agents and medicaments and serve as polymerization and copolymerization components for preparing plastics, surface coatings, paints and ion exchange materials.

8 Claims, No Drawings

PROCESS FOR PREPARING CYCLIC N-VINYLACYLAMINES

The invention relates to a process for preparing cyclic N-vinylacylamines.

It is known, from Ann. 601, 81 (1956), to prepare cyclic N-vinylacylamines by reacting cyclic arylamines with acetylene or acetylene derivatives at elevated temperatures, preferably in pressure vessels. This process has the disadvantage that extensive safety precautions and technically involved apparatus are necessary for handling the acetylene.

A process has now been found for preparing cyclic N-vinylacylamines of the formula (I)

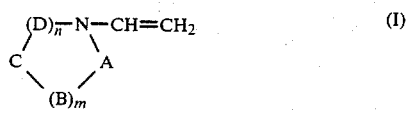

wherein
A and D denote the CO group,
B represents oxygen or the NH group,
C represents a saturated hydrocarbon radical having 1 to 3 carbon atoms or a benzene ring which can be partially or completely hydrogenated, and
m and n independently of each other denote 0 or 1 and where the number of ring members is 5 or 6, characterised in that carbonic acid esters of cyclic N-hydroxyethylacylamines of the formula (II) or (III)

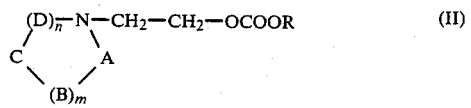

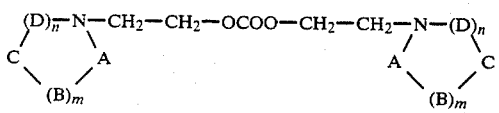

in which
A, B, C, D, m and n have the previously mentioned meaning and
R represents a saturated hydrocarbon radical having 1 to 4 carbon atoms,
are heated to temperatures of 120° to 250° C. in the presence of a catalytic amount of one or more alkali or alkaline earth metal compounds having an alkaline reaction and the reaction product is then separated off by distillation.

Saturated hydrocarbon radicals having 1 to 4, preferably 1 to 2, carbon atoms, of the formula (II), which may be mentioned are the methyl, the ethyl, the n-propyl, the isopropyl, the N-butyl, the isobutyl and the tert.-butyl radical, preferably the methyl and the ethyl radical.

Examples of carbonic acid esters of cyclic N-2-hydroxyethylacylamines which can be used in the process according to the invention are the carbonates or the alkyl carbonates, such as the methyl or ethyl carbonates, of N-2-hydroxyethylpyrrolidinone, of N-2-hydroxyethylpiperidinone, of N-2-hydroxyethyloxazolidinone, of N-2-hydroxyethyltetrahydrooxazinone, of N-2-hydroxyethylimidazolidinone, of N-2-hydroxyethylsuccinimide, of N-2-hydroxyethyltetrahydrophthalimide and of N-2-hydroxyethylhexahydrophthalimide, preferably of N-2-hydroxyethylpyrrolidinone, N-2-hydroxyethyloxazolidinone and N-2-hydroxyethylphthalimid.

The following may be mentioned as alkali or alkaline earth metal compounds having an alkaline reaction: the hydroxides, alcoholates or the salts which have an alkaline reaction, such as the carbonates or the carboxylates, of lithium, sodium, potassium, magnesium, calcium, strontium or barium. The carbonates, the carboxylates, the alcoholates or the hydroxides of sodium or of potassium are preferably used. Sodium hydroxide or potassium carbonate are particularly preferably used.

The alkali or alkaline earth metal compounds having an alkaline reaction are preferably used in amounts of 0.001 to 5% by weight, particularly preferably in amounts of 0.01 to 1% by weight, relative to the amount of the starting material.

The process according to the invention is generally carried out at temperatures of about 120° to 250° C., preferably at 140° to 220° C.

The reaction products are preferably isolated by distillation under reduced pressure, under 0.01 to 200, preferably under 0.01 to 25, mbar.

The carbonic acid esters of cyclic N-hydroxyethylacylamines to be used according to the invention are obtained in a known manner, for example by reacting N-2-hydroxyethylacylamines with carbonic acid derivatives, such as dimethyl or diethyl carbonate or by reacting dialkanolamines or aminoalkylaminoalkanols with, for example, diethyl carbonate in the presence of transesterification catalysts, such as alkali or alkaline earth metal compounds having an alkaline reaction.

The reaction proceeds in various ways, according to whether carbonates or alkyl carbonates of cyclic N-2-hydroxyethylacylamines are used as starting materials for the process according to the invention. At the reaction temperatures indicated, carbonates decarboxylate and split into mixtures of cyclic N-vinyl-acylamines (I) and cyclic N-2-hydroxyethylacylamines (IV) (see the reaction scheme below):

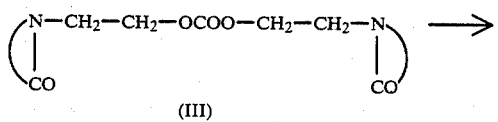

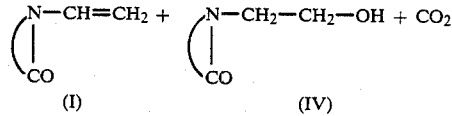

Alkyl carbonates produce instead N-vinylacylamines and alcohols (see the reaction scheme below):

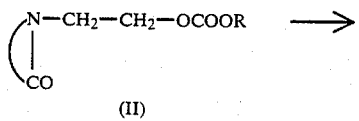

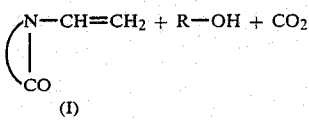

In most cases it is observed that in addition to this reaction there is also a transition from the alkyl carbonate of the cyclic N-2-hydroxyethylacylamine into the corresponding carbonate with elimination of diethyl carbonate (see the reaction scheme below):

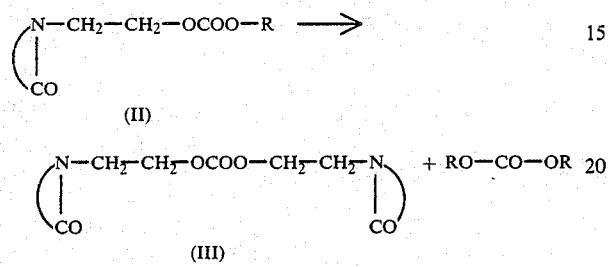

The reaction mixture therefore contains a more or less large proportion of cyclic N-2-hydroxyethylacylamines of the formula (IV).

The alcohol eliminated in the process according to the invention, for example methanol or ethanol, is advantageously trapped in a cold trap charged with dry ice, while the carbon dioxide is absorbed in a trap cooled with liquid nitrogen. The carbon dioxide can also be trapped in a suitable liquid, such as a concentrated alkali metal hydroxide solution, or in a primary amine having a high boiling point, such as aminoethanol or ethylenediamine, with carbamate formation.

The reaction products obtained by distillation according to the process according to the invention are, as stated before, as a rule mixtures of compounds of the formula (I) and (IV). These are customarily separated by fractional recrystallisation and/or by distillation. Cyclic N-2-hydroxyethylacylamines are preferably returned back into the reaction.

Cyclic N-vinylacylamines are valuable precursors in the preparation of plant protection agents and medicaments and serve as polymerisation and copolymerisation components for preparing plastics, surface coatings, paints and ion exchange materials (compare, for example, U.S. Pat. No. 2,276,840, German No. 832,437, U.S. Pat. No. 2,818,362 and Ullmanns Encycl. Techn. Chem. [Ullmann's Encyclopaedia of Industrial Chemistry] 4th edition (1972) volume 19, 385 (1980).

The examples which follow are intended to illustrate the preparation of cyclic N-vinylacylamines and their use for preparing ion exchange materials.

I. Preparation of cyclic N-vinylacylamines

EXAMPLE 1

(a) N-2-Oxazolidinonylethylethyl carbonate 210 g (2 mols) of diethanolamine, 1,180 g (10 mols) of diethyl carbonate and 2 g of potassium carbonate are heated with stirring for 2 hours in a packed column at an internal temperature of 102° to 130° C., while 270 g of alcohol are split off via the top. The catalyst is removed by allowing the reaction product to flow over a column packed with 200 g of an ion exchange material, a sulphonated polystyrene resin. After excess diethyl carbonate has been distilled off, N-2-oxazolidinonylethylethyl carbonate is distilled at 130° to 133° C./0.02 mbar. Yield: 375 g=92% of theory; melting point: 32° to 33° C.

(b) N-Vinyloxazolidinone 60 g of the reaction product of (a) are heated under a pressure of 0.03 mbar to an internal temperature of 136° to 160° C., after 5 mg of sodium hydroxide have been added, while carbon dioxide is split off in a lively manner and colourless distillate (16 g) passes over at 100° to 136° C. A mixture of ethanol and diethyl carbonate is trapped in a cold trap supplied with dry ice, while the carbon dioxide is trapped in a cold trap containing liquid nitrogen. The distillation residue (25 g) crystallizes on cooling down. Melting point: 107° C. The residue consists of di-(N-2-oxazolidinonylethyl)carbonate. Redistillation produces at 60° to 62° C./0.01 mbar 12 g of N-vinyloxazolidinone; $n_D^{20}=1.4970$; melting point: $-6°$ C.

EXAMPLE 2

(a) Di-(N-2-oxazolidinonylethyl)carbonate 1,650 g (16 mols) of diethanolamine, 3,115 g (26.4 mols) of diethyl carbonate and 4 g of potassium carbonate are heated in a 1.10 m long packed column for 7 hours at an internal temperature of 105° to 132° C., until 1,884 g of ethanol have distilled off via the top. The remainder of the alcohol (315 g) is separated off by reducing the pressure in stages down to 80 mbar. After excess diethyl carbonate has been distilled off under 30 mbar, 2,370 g of residue, which consists of almost pure di-(N-2-oxazolidinonylethyl)carbonate, are obtained.

Melting point: 107° C. (recrystallized from ethyl acetate), boiling point: 230° C./0.01 mbar. $C_{11}H_{16}N_2O_7$ (288.2)

Calculated: C 45.83, H 5.56, N 9.72. Found: C 45.7, H 5.62, N 9.69.

(b) N-Vinyloxazolidinone 295 g of the product obtained according to (a) are added dropwise under a pressure of 0.03 mbar in the course of 4 hours to a heated stirred flask at 190° C., while the reaction product passes over at 140° to 160° C. The carbon dioxide is trapped in a trap cooled with liquid nitrogen. The amount of the distillate is 210 g, and the amount of carbon dioxide is 41 g. Redistillation produces 2 fractions, at 80° to 85° C./0.01 mbar 102 g of N-vinyloxazolidinone and at 145° to 156° C./0.01 mbar 103 g of N-2-hydroxyethyloxazolidinone. Yield of N-vinyloxazolidinone: 90% of theory; $n_D^{20}=1.4968$. N-2-Hydroxyethyloxazolidinone obtained simultaneously and having a melting point of 32° to 33° C. and an $n_D^{20}=1.4830$, can be re-reacted with diethyl carbonate to give di-(N-2-oxazolidinonylethyl)carbonate.

EXAMPLE 3

(a) Hydroxyethylphthalimide 888 g (6 mols) of phthalic anhydride are added in portions to 412.5 g of 98% strength ethanolamine (6.6 mols), and the mixture is heated in the course of 2 hours from 110° to 190° C., until 114 g of water have been distilled off. Excess ethanolamine is then removed under reduced pressure down to 145° C./0.1 mbar. The yield is quantitative: 1,145 g.

(b) N-2-Phthalimidylethylethyl carbonate 1,145 g (6 mols) of hydroxyethylphthalimide, 2,832 g (24 mols) of diethyl carbonate and 3 g of potassium carbonate are heated for 3.5 hours in the same apparatus as in Example 2(a) at an internal temperature of 127° to 140° C., until 276 g of ethanol have been separated off via the top. 2,200 g of diethyl carbonate are then distilled off under reduced pressure (200–30 mbar) at an internal temperature of up to 125° C., and 1,525 g of a crystallized residue which essentially consists of N-2-phthalimidylethylethyl carbonate are obtained. Melting point: 106° C. (recrystallized from toluene).

(c) N-Vinylphthalimide

The product of (b) is heated in a flask equipped with a wide Claisen bridge to an internal temperature of 160° to 200° C. while alcohol, diethyl carbonate and carbon dioxide are split off and a distillate which solidifies in the receiving flask passes over at 140° to 160° C./0.07 mbar. The distillate (950 g) is dissolved in 3 times the amount of toluene. On cooling the solution, N-2-hydroxyethylphthalimide precipitates. The filtrate is redistilled after 5 g of copper powder have been added. 503 g of N-vinylphthalimide are obtained at 90° to 95° C./0.04 mbar; melting point: 80° C. A further fraction which passes over at 151° to 153° C./0.04 mbar consists of hydroxyethylphthalimide. 400 g of hydroxyethylphthalimide are recovered in total. Yield of N-vinylphthalimide, relative to hydroxyethylphthalimide reacted: 75%.

EXAMPLE 4

(a) N-2-Hydroxyethylethyleneurea (N-2-hydroxyethylimidazolidinone)

104 g (1 mol) of 2-(2-aminoethylamino)-ethanol and 60 g of urea are heated at 90° to 230° C. until the elimination of ammonia is complete, and N-2-hydroxyethylimidazolidinone is obtained in the yield calculated.

(b) N-Vinylimidazolidinone 130 g (1 mol) of N-2-hydroxyethylimidazolidinone, 472 g (4 mols) of diethyl carbonate and 1 g of potassium carbonate was heated as in Example 2(a) to 110° to 130° C., at the end under 400 mbar, until the amount of ethanol calculated has been split off. The reaction product is filtered and freed from excess diethyl carbonate under 220 mbar. The residue (125 g) is heated after 2 g of copper powder have been added, to 200° to 210° C./0.04 mbar while carbon dioxide and ethanol are split off and a partially crystallized distillate passes over at 140° to 150° C./0.04 mbar. Redistillation produces 12 g of N-vinylimidazolidinone at 104° to 116° C./0.04 mbar. Melting point: 77° to 79° C. (recrystallized from a small amount of methanol).

EXAMPLE 5

(a) N-2-Hydroxyethylpyrrolidinone 430 g (5 mols) of butyrolacetone are allowed to flow with mild cooling into 403 g (6.5 mols) of aminoethanol, and the water of reaction and excess aminoethanol are driven over for 36 hours by heating to 180° to 190° C., at the end under 20 mbar. 550 g (=85% of theory) of hydroxyethylpyrrolidinone, $n_D^{20}=1.4950$, pass over at 119° to 123° C./0.02 mbar.

(b) N-2-Pyrrolidinonylethylethyl carbonate 258 g (2 mols) of hydroxyethylpyrrolidinone, 708 g (6 mols) of diethyl carbonate and 1 g of potassium carbonate are heated as in Example 1(a) to 110° to 130° C. and the amount of alcohol calculated is allowed to pass over via the top. Non-converted diethyl carbonate is removed under reduced pressure up to 130° C. 380 g of N-2-pyrrolidinonylethylethyl carbonate having a boiling point of 98° C./0.02 mbar and an $n_D^{20}=1.4656$ are obtained.

(c) N-Vinylpyrrolidinone

The product of (b) is heated for 11 hours under 20 mbar at 150° to 160° C., and 220 g of distillate are separated off at 90° to 160° C. Redistillation via a 15 cm long Vigreux column produces 30 g of diethyl carbonate having a boiling point of 24° to 27° C./16 mbar, 92 g of N-vinylpyrrolidinone, 92° to 93° C./16 mbar, and 42 g of hydroxyethylpyrrolidinone, 112° to 116° C./0.24 mbar. Yield: 50%, relative to hydroxyethylpyrrolidinone reacted.

II. Use of cyclic vinylacylamines for preparing ion exchange materials (demonstrated by the example of N-vinylphthalimide)

Preparation of bead polymers

EXAMPLE 6

500 ml of distilled water and 0.27 g of methyl-cellulose are initially introduced into a reaction vessel equipped with a thermometer, stirrer and reflux condenser, and heated to 60° C. A dissolved organic phase consisting of 70 g of N-vinylphthalimide, 12.3 g of 63.5% strength divinylbenzene, 1,225 g of azobisisobutyronitrile and 30 ml of dichloroethane is added with stirring. The batch is polymerized for 3 hours at 60° C. and for 16 hours at 80° C. After the polymerization is complete, the bead polymer formed is filtered off with suction and thoroughly washed with distilled water and methanol. Dry yield: 80.7 g=98.06% by weight.

EXAMPLE 7

77 ml of distilled water and 0.077 g of methylcellulose are initially introduced into a reaction vessel equipped with a thermometer, stirrer and reflux condenser, and heated to 60° C. A dissolved organic phase consisting of 20 g of N-vinylphthalimide, 3 g of 63.5% strength divinylbenzene, 1 g of styrene, 0.35 g of azobisisobutyronitrile and 10 ml of dichloroethane is added with stirring. The batch is polymerized for 3 hours at 60° C. and for 16 hours at 80° C. After the polymerization is complete, the bead polymer formed is filtered off with suction and thoroughly washed with distilled water and methanol. Dry yield: 21.2 g≙88.33% by weight.

EXAMPLE 8

77 ml of distilled water, 0.077 g of methylcellulose and 0.01 g of $NaNO_2$ are initially introduced into a reaction vessel equipped with a thermometer, stirrer and reflux condenser, and heated to 60° C. A dissolved organic phase consisting of 20 g of N-vinylphthalimide, 3.5 g of 63.5% strength divinylbenzene, 0.35 g of azobisisobutyronitrile and 10 ml of dichloroethane is added with stirring. The batch is polymerized for 3 hours at 60° C., 12 hours at 80° C. and 4 hours at 90° C. After the polymerization is complete, the bead polymer formed is filtered off with suction and thoroughly washed with distilled water and methanol. Dry yield: 94.8% by weight.

Hydrolysis of the bead polymers

EXAMPLE 9

100 g of hydrazine hydrate (64% by weight strength) are added to 30 g of the bead polymer prepared according to Example 6, and the mixture is allowed to swell for 2 hours and is then heated at the reflux temperature for 24 hours. 10.2 g of hydrazinolyzed exchange material are formed. The exchange material has a weakly basic total capacity of 11.72 meq/g and a weakly acidic total capacity of 1.64 meq/g.

EXAMPLE 10

300 g of 20% strength sodium hydroxide solution are added to 30 g of the bead polymer prepared according to Example 6, and the mixture is allowed to swell overnight and is heated in an autoclave at 100° C. for 1 hour and for a further hour at 180° C., and kept at this temperature for 4 hours. 22.8 g of exchange material having a weakly basic total capacity of 0.598 Eq/l and a weakly acidic capacity of 0.97 Eq/l are obtained.

What is claimed is:

1. A process for preparing a cyclic N-vinylacylamine of the formula (I)

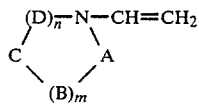 (I)

wherein
A and D denote the CO group,
B represents oxygen or the NH group,
C represents a saturated hydrocarbon radical having 1 to 3 carbon atoms or a benzene ring which can be partially or completely hydrogenated, and
m and n independently of each other denote 0 or 1
and where the number of ring members is 5 or 6, which comprises heating a carbonic acid ester of a cyclic N-hydroxyethylacylamine of either formula (II) or (III) below

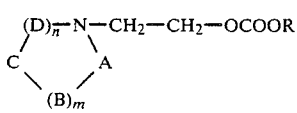 (II)

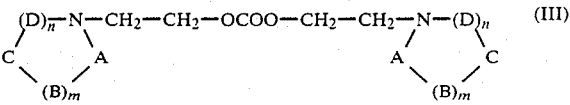 (III)

in which
A, B, C, D m and n have the previously assigned significance and
R represents a saturated hydrocarbon radical having 1 to 4 carbon atoms, at a temperature of 120° to 250° C. in the presence of a catalytic amount of at least one alkali or alkaline earth metal compound having an alkaline reaction and thereafter separating off the reaction product by distillation.

2. A process according to claim 1 wherein a compound of the formula below is heated

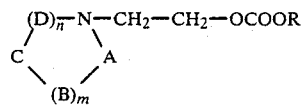 (II)

in which
A, B, C, D, R, m and n have the previously assigned significance.

3. A process according to claim 1 wherein a compound of the formula below is heated

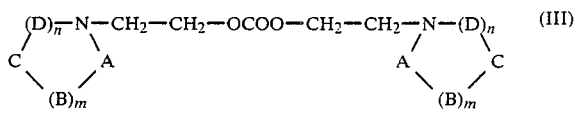 (III)

in which
A, B, C, D, R, m and n have the previously assigned significance.

4. A process according to claim 1 wherein a carbonate or an alkyl carbonate of N-2-hydroxyethylpyrrolidinone or of N-2-hydroxyalkyloxazolidinone or of N-2-hydroxyalkylphthalamide is employed as a carbonic acid ester of a cyclic N-2-hydroxyethylacylamine and the same is heated at a temperature of 120° to 250° C.

5. A process according to claim 1 wherein the process is carried out at a temperature of 140° to 220° C.

6. A process according to claim 1 wherein the alkali or alkaline earth metal compound having an alkaline reaction is a hydroxide, alcoholate, carbonate or carboxylate of sodium or of potassium.

7. A process according to claim 1 wherein said alkali or alkaline earth metal compound having an alkaline reaction is employed in an amount of 0.001 to 5% by weight.

8. A process according to claim 1 wherein the reaction product is distilled off under a reduced pressure of 0.01 to 200 m bar.

* * * * *